(12) United States Patent
Schornstein et al.

(10) Patent No.: US 12,078,626 B2
(45) Date of Patent: Sep. 3, 2024

(54) METHOD AND KIT FOR DETECTING DIESEL EXHAUST FLUID IN FUEL

(71) Applicant: Acustrip Company, Inc., Denville, NJ (US)

(72) Inventors: Ronald Schornstein, Mountain Lakes, NJ (US); Samuel D'Arcangelis, Randolph, NJ (US)

(73) Assignee: Acustrip Company, Inc., Denville, NJ (US)

( * ) Notice: Subject to any disclaimer, the term of this patent is extended or adjusted under 35 U.S.C. 154(b) by 0 days.

(21) Appl. No.: 18/214,084

(22) Filed: Jun. 26, 2023

(65) Prior Publication Data

US 2023/0341362 A1    Oct. 26, 2023

Related U.S. Application Data

(62) Division of application No. 17/093,840, filed on Nov. 10, 2020, now Pat. No. 11,726,070.

(51) Int. Cl.
*G01N 31/22*    (2006.01)
*G01N 33/22*    (2006.01)

(52) U.S. Cl.
CPC .......... *G01N 31/22* (2013.01); *G01N 33/22* (2013.01)

(58) Field of Classification Search
None
See application file for complete search history.

(56) References Cited

U.S. PATENT DOCUMENTS

| | | |
|---|---|---|
| 3,467,499 A | 9/1969 | Woodbridge |
| 3,926,734 A | 12/1975 | Gray |
| 2018/0024073 A1 | 1/2018 | Schornstein |
| 2021/0072161 A1 | 3/2021 | Case |

OTHER PUBLICATIONS

Industrial Test Systems, "AquariaTest™ 1—Ammonia—25 tests | ITS-483343", 2016, available at: https://www.moti-vitality.com/product/aquariatest-1-ammonia25-tests/ (2 pages).

*Primary Examiner* — Jennifer Wecker
*Assistant Examiner* — Kathryn Elizabeth Limbaugh
(74) *Attorney, Agent, or Firm* — Hoffmann & Baron, LLP

(57) ABSTRACT

A method and kit for detecting the presence of diesel exhaust fluid in fuel is disclosed. The method includes obtaining a fuel sample, combining the fuel sample with a buffered urease solution to make a test solution, agitating the test solution, allowing the test solution to separate into layers and convert urea to ammonia. The method also includes adjusting a pH of the aqueous layer of the test solution, isolating the aqueous layer, immersing, agitating and then removing a reagent strip, and allowing the aqueous layer to develop a color change for an indication of presence of ammonia from any DEF contamination.

11 Claims, 4 Drawing Sheets
(3 of 4 Drawing Sheet(s) Filed in Color)

METHOD AND KIT FOR DETECTING DIESEL EXHAUST FLUID IN FUEL

CROSS-REFERENCE TO RELATED APPLICATIONS

This application is a divisional of U.S. application Ser. No. 17/093,840, filed Nov. 10, 2020, the contents of which is incorporated herein by reference in their entirety.

FIELD OF THE INVENTION

The present invention relates to methods and kits for detecting diesel exhaust fluid in a fuel.

BACKGROUND

Diesel Exhaust Fluid (DEF) is a colorless fluid used with diesel engines to reduce the amount of air pollution and emissions exhausted from vehicles such as aircrafts and automobiles. Specifically, DEF is a non-hazardous fluid that is added to the exhaust systems of diesel vehicles to break down emissions into water and nitrogen. While DEF itself is not harmful to the environment, a mixture of water and urea contained in DEF can result in the formation of crystals that can block fuel filters, thus, damaging engines and causing engine failure. Thus, DEF should never be used as an additive for any fuel (diesel or aircraft). DEF is an aqueous urea solution made with 32.5% urea and 67.5% deionized water. Typically, DEF is stored in a specialized tank on the chassis of diesel engine vehicles, that is then injected into the engine exhaust to promote break down of noxious emissions (e.g., nitrogen oxides) into harmless nitrogen and water. The DEF contamination occurs because the urea in DEF reacts with certain fuel chemical components to form crystalline deposits in the fuel system. These deposits then flow through the fuel system (e.g., aircraft fuel system) and accumulate on fuel filters and other fuel system components, which can and has led to inflight engine failures. Unfortunately, there have been aircraft engine failure incidents due to DEF contamination of fuel supply.

Investigations of these incidents have discovered that the most common cause of DEF contamination in fuel is ground crew members confusing the DEF with the additive Fuel System Icing Inhibitor (FSII). Both liquids are clear and colorless. They can be stored in similar containers and are often stored in close proximity to each other. Thus, crew members can easily make a mistake by using DEF instead of FSII.

Accordingly, there exists a need for a method for detecting DEF contamination of a fuel to, in part, prevent damage to engine and engine failure.

SUMMARY

A method is provided for detecting diesel exhaust fluid in fuel. The method includes the steps of: i) obtaining a fuel sample to be tested from the fuel; ii) combining the fuel sample with a buffered urease solution to make a test solution; iii) agitating the test solution to extract urea; iv) allowing the test solution to separate into layers and developing an aqueous layer to convert any urea from DEF, if present, into ammonia; v) adjusting a pH of the aqueous layer to greater than or equal to about 11; vi) contacting a reagent strip with the aqueous layer; and vii) developing a color change of the aqueous layer to detect a presence of ammonia. The buffered urease solution may have a pH of about 6.8 to about 7.8, or about 7.4 to about 7.6, and comprise urease and sodium phosphate buffer. The step of adjusting the pH of the aqueous layer of the test solution may comprise: adding a pH adjustment solution to the test solution to adjust the pH of the aqueous layer, agitating the test solution, and allowing the test solution to separate into layers, and optionally the pH adjustment solution is added to adjust the pH of the aqueous layer to about 11. The reagent strip may comprise solid bleach, an iron (III) cyano complex, such as, but not limited to a nitroprusside or ferricyanide salt, and salicylic acid. The step of separating and developing the aqueous layer to convert urea into ammonia may be about 3 minutes to about 15 minutes. The step of contacting the reagent strip with the aqueous layer may comprise immersing the reagent strip in the aqueous layer, and/or agitating the strip in the aqueous layer for about 50 to about 90 seconds. The step of developing the color change may be about 2 minutes to about 10 minutes, or about 3 minutes to about 5 minutes.

A kit for detecting diesel exhaust fluid in fuel is also disclosed. The kit comprises: a buffered urease solution for mixing with a fuel sample to make a test solution, a plurality of pH test strips for determining a pH of an aqueous layer of the test solution, a pH adjustment solution for adjusting the pH of an aqueous layer, and a plurality of reagent strips for reacting with the aqueous layer. The buffered urease solution may have a pH of about 6.8 to about 7.8, or about 7.4, and comprise urease and sodium phosphate buffer, and/or the reagent strip may comprise solid bleach, an iron (III) cyano complex, such as, but not limited to a nitroprusside or ferricyanide salt, and salicylic acid.

The kit may also include a plurality of heavy metal test strips. The kit may also include a color legend, one or more vials, and/or one or more pipettes.

BRIEF DESCRIPTION OF THE DRAWINGS

The patent or application file contains at least one drawing executed in color. Copies of this patent or patent application publication with color drawing(s) will be provided by the Office upon request and payment of the necessary fee. Some embodiments or aspects are illustrated by way of non-limiting example.

DETAILED DESCRIPTION

Figure 1:
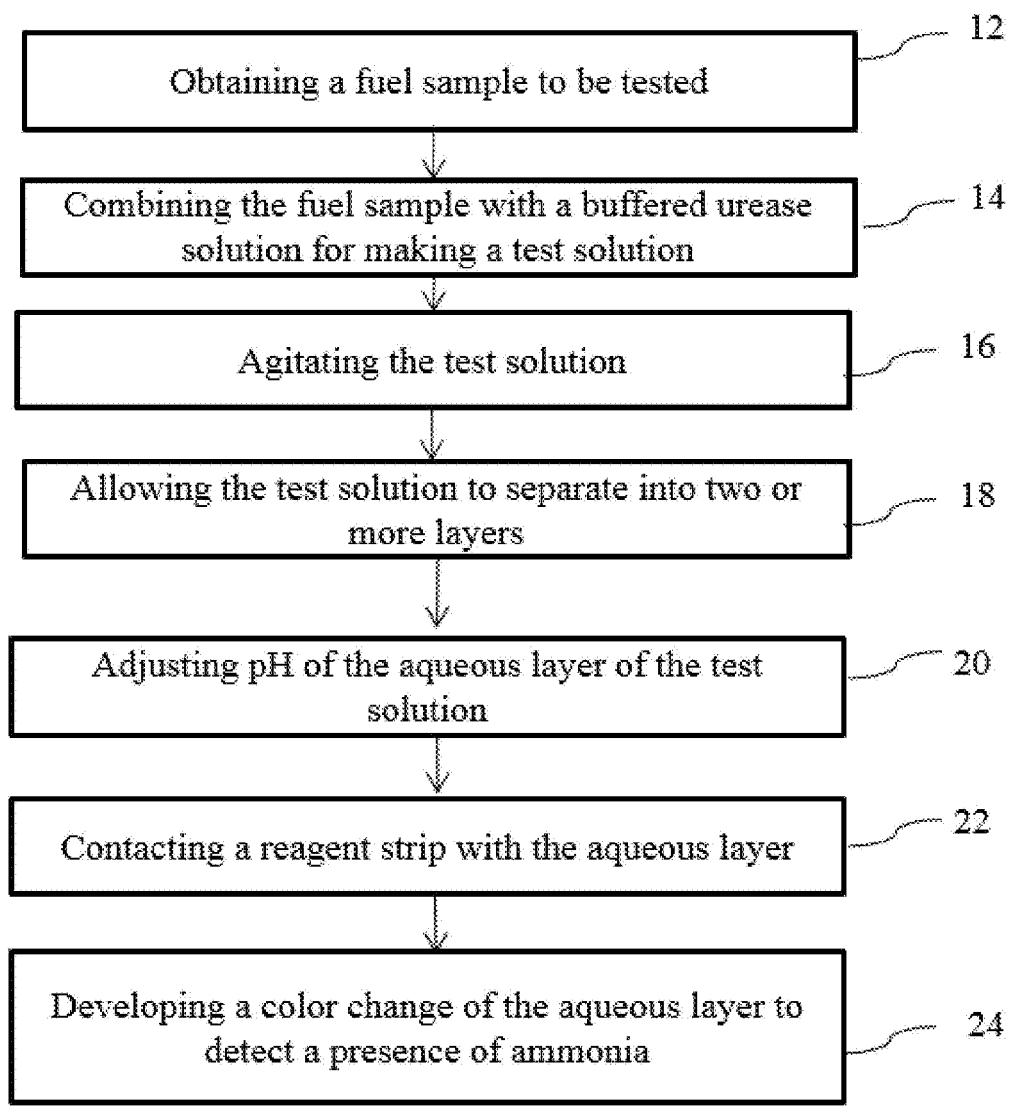
FIG. 1 is a flowchart of a method for detecting diesel exhaust fluid in fuel.

Principles of the present disclosure will be described herein in the context of an illustrative method and kit for detecting diesel exhaust fluid in fuel. It is to be appreciated, however, that the specific embodiments and/or methods illustratively shown and described herein are to be considered exemplary as opposed to limiting. Moreover, it will become apparent to those skilled in the art given the teachings herein that numerous modifications can be made to the embodiments shown that are within the scope of the claims. That is, no limitations with respect to the embodiments shown and described herein are intended or should be inferred.

The method and kit described herein provide a means for detecting the presence of DEF in fuel by using a number of steps and reactions. The first reaction converts urea from the DEF into ammonia. In the second series of reactions, the ammonia is converted to chloramine. The chloramine, in turn, reacts with salicylate reagent to form an aniline precursor, catalyzed by an iron (III) cyano complex, such as, but not limited to a nitroprusside or ferricyanide salt, which then reacts with oxygen in the air to develop an azo compound (dye). Thus, if the test solution displays a color change to green or blue after completion of the series of reactions, the tested fuel is considered to be contaminated with DEF.

A method for detecting DEF in fuel is disclosed. DEF is typically stored in a specialized tank on the chassis of diesel engine vehicles, that is then injected into the engine exhaust to promote break down of noxious emissions (e.g., nitrogen oxides) into harmless nitrogen and water. Non-limiting examples of fuel that may be tested with the method described herein include aviation fuel and diesel fuel.

A fuel sample to be tested for detecting DEF in fuel may be obtained from the fuel stored in a fuel storage (e.g., a fuel tank). The fuel sample may be at least about 5 ml, at least about 6 ml, about 6 ml to about 20 ml, or about 6 ml. The fuel sample may be taken from the bottom of the fuel storage for testing DEF contamination of the fuel. Once the fuel sample is obtained from the fuel tank, it may be placed in a container such as a glass container, for temporarily storing the fuel sample.

The fuel sample is combined with a buffered urease solution to prepare a test solution for detecting DEF in the fuel. The buffered urease solution has a pH of about 6.8 to about 7.8, about 6.8 to about 7.6, about 7.4 to about 7.6, about 7.4, or about 7.6. The buffered urease solution may be prepared with urease and sodium phosphate buffer (or other suitable buffer, such as an acetic acid/acetate system) in distilled water. The buffered urease solution may be adjusted with an acid, such as concentrated phosphoric acid ($H_3PO_4$, 85 wt %), to a pH of about 6.8 to about 7.8, about 6.8 to about 7.6, about 7.4 to about 7.6, about 7.4, or about 7.6. The buffered urease solution may be about 50 ppm to about 700 ppm, about 60 ppm to about 400 ppm, about 70 ppm to about 300 ppm, or about 100 ppm urease buffered in about 0.10 M to about 0.05 M, or about 0.05 M phosphate. In an embodiment, about 100 ppm urease buffered in about 0.10 M to about 0.05 M, or about 0.05 M phosphate, at a pH of about 6.8 to about 7.6, about 7.4, or about 7.6 is added to the fuel sample.

The test solution may be prepared in a laboratory container, such as a vial, by mixing a sufficient amount of the fuel sample with a sufficient amount of the buffered urease solution. The amount of buffered urease solution mixed with the fuel sample may be about 1 ml to about 10 ml, about 1 ml to about 5 ml, or about 2 ml. In an embodiment, about 6 mL of the fuel sample is mixed with about 2 mL of the buffered urease solution to prepare a test solution.

The test solution is agitated for a sufficient time for thoroughly mixing the fuel sample and the buffered urease solution. This agitating may be performed for an amount of time to allow the buffered urease solution to mix with the fuel sample. The mixing time may be about 10 seconds to about 10 minutes, about 10 seconds to about 3 minutes, about 10 seconds to about 1 minute, or about 10 seconds to about 30 seconds. The agitating may be performed by any means, for example, by shaking vigorously by hand or by using any machine known in the art.

After agitation, the test solution is allowed to rest and settle for a sufficient time to allow the solution to separate into two or more layers with an aqueous (clear) layer forming at the bottom of the test solution. The test solution is also allowed time to develop. If DEF is present in the fuel sample, the reaction of the fuel sample with the buffered urease solution causes the urea in the DEF to convert to ammonia. The time required to separate and develop may be about 30 seconds to about 15 minutes, about 30 seconds to about 3 minutes, about 1 minute to about 10 minutes, about 1 minute to about 3 minutes, about 1 minute, about 2 minutes, about 3 minutes, about 5 minutes, or about 10 minutes. The time needed to complete development and conversion to ammonia depends on the exact pH of the sample and the room temperature, as understood by one of ordinary skill in the art.

The time required to separate into layers may be about 15 seconds to about 3 minutes. The time required to develop after separating may be about 3 to about 30 minutes, about 3 to about 15 minutes, about 3 to about 10 minutes, about 3 minutes, about 5 minutes, or about 10 minutes.

In an embodiment, the buffered urease solution converts urea (of DEF in the fuel sample) to ammonia at a pH between 6.8 and 7.8 according to the following reaction:

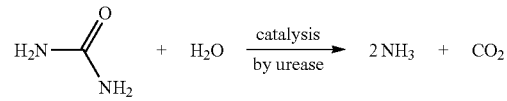

No liberation of $CO_2$ is observed and most of the ammonia stays in the solution as ammonium ion at pH 7.4. The time to complete this conversion may be about 3 to about 10 minutes, or less than about 5 minutes at room temperature.

Optionally, a portion of the aqueous layer may be tested for the presence of heavy metals and a pH of between about 7 and about 8 because metals and a pH outside of this range may interfere with the foregoing development step (i.e., the conversion of urea to ammonia). If the aqueous layer contains heavy metals or has an incompatible pH (i.e., below about 7 or above about 8), then it may need to be serviced before proceeding to the next step of adjusting the pH to greater than or equal to about 11 and completing the test for DEF contamination.

A heavy metal test determines the presence of any heavy metals in the aqueous layer. The heavy metal test may be conducted by contacting a few drops of the aqueous layer of the test solution with a heavy metal test strip. Any heavy metal test strip known in the art may be used, for example, the SenSafe Water Metal Check available in the market. If the heavy metal test strip indicates that the aqueous layer contains heavy metals, the test solution is not ready to be tested for DEF contamination, and the fuel needs to be serviced to remove the heavy metals.

A testing of the pH of the aqueous layer may be conducted by contacting a few drops of the aqueous layer of the test solution with a pH test strip. Any pH test strip or pH paper known in the art may be used. If the pH test strip indicates the pH of the aqueous layer is less than 7 or greater than 8, then the test solution is not ready to be tested for DEF contamination, and the fuel should be serviced.

When performed, when the heavy metal test shows that no heavy metals are present and the pH test shows that the aqueous layer has a pH between about 7 and about 8, then the method may proceed with the next steps for detecting DEF contamination.

After awaiting sufficient time to allow the development of any urea, if present, to ammonia, the method comprises adjusting a pH of the aqueous layer to greater than or equal to about 11, about 11 to about 14, or about 11. The pH is adjusted to the correct basicity (e.g., pH=11) using a pH adjustment solution. The urease is destroyed (irreversibly inactivated), and ammonium in the solution is now clearly converted through equilibrium to ammonia. The pH adjustment solution may be any known pH adjustment solution, e.g., the pH adjustment solution included in the Ammonia AquariaTest kit (#483343) that is commercially available.

The mixture may then be agitated by any means and allowed to settle to separate into two or more layers. The aqueous layer of the test solution is tested with a pH test strip or any other device known to determine pH, such a pH test paper, to determine the pH of the aqueous layer. If the pH is less than about 11, another drop or more of the pH adjustment solution may be added to the mixture, agitated, and tested again. This is repeated until the pH of the aqueous layer is greater than or equal to about 11.

In an embodiment, the step of adjusting the pH of the aqueous layer of the test solution comprises: adding a pH adjustment solution to the test solution to adjust the pH of the aqueous layer, agitating the test solution, and allowing the test solution to separate into layers. Agitating may be done by may means known in the art for the amount of time needed to thoroughly mix the solution.

Optionally, the aqueous layer may be isolated from the test solution to be tested for DEF contamination of the fuel. The aqueous layer at the bottom of the test solution may be transferred to a clean container (e.g., vial) by any means known in the art, for example, by using a laboratory tool for transporting a volume of liquid, such as pipette.

After adjusting the pH, the method comprises contacting a reagent strip with the aqueous layer, and, optionally, the aqueous solution is agitated for a sufficient time for the reagent strip to release its reagents into the aqueous layer. The amount of time for mixing may be about 50 seconds to about 3 minutes, about 60 seconds to about 3 minutes, about 50 seconds to about 2 minutes, about 50 to about 70 seconds, at least about 60 seconds, or about 60 seconds.

The reagent strip may include a combination of solid bleach, an iron (III) cyano complex, and salicylic acid. The iron (III) cyano complex may be, but is not limited to, a nitroprusside, for example sodium nitroprusside, or a ferricyanide salt, for example potassium ferricyanide. Each of these components may be individually placed on and adhered to the stick or central structure in individual units, such as pads or blocks, and formulated so that when the strip is brought into contact with a liquid, the reagents dissolve into the solution and react. The hypochlorite ion reacts with any available ammonia to generate chloramine. Chloramine in turn reacts with salicylic acid with catalytic help from the iron (III) cyano anion, to form aminosalicylic acid. With development time during exposure to atmospheric oxygen, the aminosalicylic acid auto-oxidizes to form a characteristically blue azo dye. In the yellow test solution, the blue azo dye makes the solution turn green, when there is ammonia present, yielding a positive indication. The response of increasing ammonia to the depth of the green color is essentially linear. The salicylic acid is present in an amount approximately four times more by weight than the amount that is needed to complete the reaction so that it is hypochlorite, not salicylic acid, that is the limiting reagent.

Each reagent strip may include about 8 micromoles (480 micrograms) to about 20 micromoles (1,200 micrograms) of available hypochlorite ion (either as the sodium or calcium salt), about 8 micromoles (1,600 micrograms) to about 20 micromoles (4,000 micrograms) of available iron (III) compound (e.g., iron (III) ferricyanide), and about 30 micromoles (4500 micrograms) to about 80 micromoles (12,000 micrograms) of available salicylic acid. Each reagent strip may include about 10 micromoles (600 micrograms) to about 15 micromoles (900 micrograms) of available hypochlorite ion (either as the sodium or calcium salt), about 10 micromoles (2,000 micrograms) to about 15 micromoles (3,000 micrograms) of available iron (III) compound, and about 40 micromoles (6,000 micrograms) to about 75 micromoles (11,000 micrograms) of available salicylic acid. Each reagent strip may include about 8 micromoles (480 micrograms) to about 12 micromoles (720 micrograms) of available hypochlorite ion (either as the sodium or calcium salt), about 8 micromoles (1,600 micrograms) to about 12 micromoles (2,400 micrograms) of available iron (III) compound, and about 30 micromoles (4,500 micrograms) to about 60 micromoles (9,000 micrograms) of available salicylic acid. Each reagent strip may include about 10 micromoles (600 micrograms) of available hypochlorite ion (either as the sodium or calcium salt), about 10 micromoles (2,000 micrograms) of available iron (III) compound, and about 40 micromoles (6,000 micrograms) of available salicylic acid.

After agitation, the reagent strip is removed from the aqueous layer, and the reagents from the reagent strip are allow to react with the aqueous layer to develop a color change for an indication of the presence of ammonia. If the aqueous layer contains ammonia, the ammonia is converted to chloramine by bleach from the reagent strip. Then, the chloramine reacts with salicylic acid from the reagent strip to form an aniline precursor. The reaction is catalyzed by the iron (III) ferricyanide complex or nitroprusside to speed up the reaction. A color change may develop in about 2 minutes to about 10 minutes, about 3 minutes to about 5 minutes, or about 3 minutes, after the agitation. The color change of green or blue indicates that ammonia is present in the aqueous layer. This shows that the fuel contains urea from DEF, and the fuel is contaminated with DEF. The color change to yellow indicates that ammonia is not present in the aqueous layer and thus, no urea (or DEF) is present in the fuel.

In an embodiment, the reagent strip is inserted into the test sample, and reagents included in the reagent strip are released simultaneously into the solution over about 60 seconds of agitation. The reagent strip is comprised of solid bleach, an iron (III) cyano complex, and salicylic acid. The ammonia is converted to chloramine by the liberated bleach:

$$NH_3 + NaOCl \rightarrow NH_2Cl + NaOH$$

Chloramine, in turn, reacts with salicylate reagent liberated from the reagent strip to form the aniline precursor below:

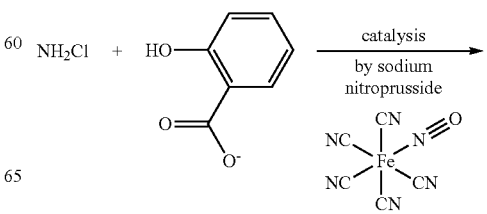

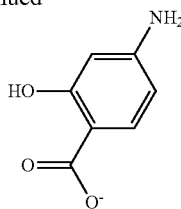

The reaction is catalyzed by the iron (III) cyano complex, for example, sodium nitroprusside, which is added in excess to speed up the reaction. The product of oxidative coupling of a pair of the anilines is shown below. Enough oxygen is required for this reaction to occur. Thus, during the color development phase of the test, the vials may be left open, such that the following reaction occurs:

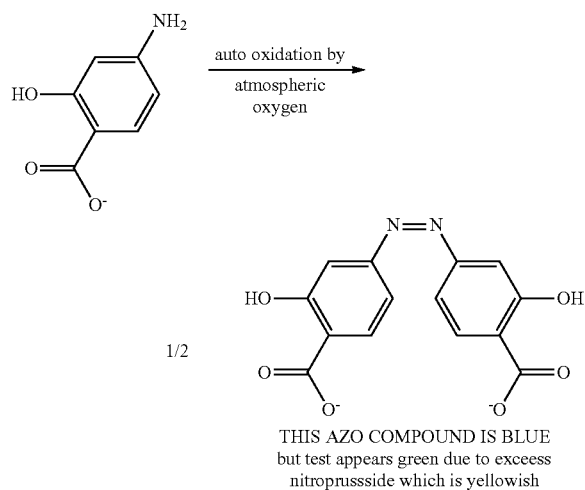

The test measures ppm urea which produces a trace (up to 5 ppm urea), positive (greater than 5 ppm urea), or negative (no urea) results. The trace, positive, and negative results are indicated with shades of green, dark green, and yellow, respectively.

The test may be a positive or negative trace test (that is to say up to 5 ppm urea detectible as the urea-trace condition (shades of green on the color legend) and greater than 5 ppm as a urea-positive condition (dark green/too dark to measure on the legend), and "urea not detected" for the urea-negative condition (yellow, with no green). The legend may provide the same information, except that instead of ammonia the legend may be marked in terms of ppm urea detected. In such an embodiment, the darkest square would be greater or equal to 5 ppm ($\geq 5$ ppm). The test should be sensitive enough to determine such small quantities of urea and only be qualitative above such small amounts in case the urease becomes inhibited by conditions in the fuel, even the slightest activity will produce a green color. Aviation fuel should have absolutely no urea in it.

Figure 7:
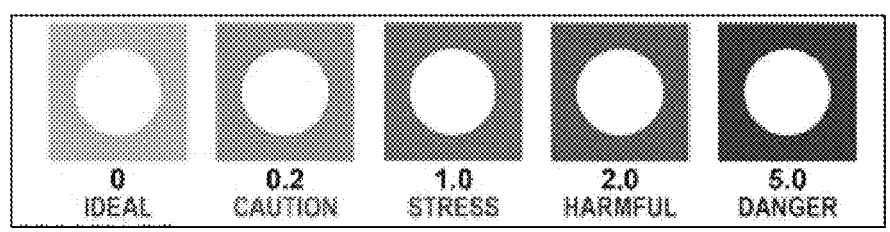
FIG. 7 is an exemplary color legend.

The method according to the disclosure may include a step of comparing the color of the aqueous layer to the color legend. A non-limiting example of a color legend in accordance with this disclosure is shown in FIG. 7.

An example of this method is shown in a non-limiting flow chart of FIG. 1. FIG. 1 demonstrates a method including the steps of obtaining a fuel sample to be tested 12, then combining the fuel sample with a buffered urease solution to make a test solution 14, then agitating the solution 16, followed by allowing the test solution to separate into two or more layers 18, including an aqueous layer. Next, the pH of the aqueous layer is adjusted 20, followed by contacting a reagent strip with the aqueous layer 22, and lastly developing a color change of the aqueous layer 24.

A yellow color indicates there is no detectible urea. Any shade of green color indicates the presence of urea. The color legend may present a scale of yellow to green with the shade of green getting darker as greater amounts of urea are detected in the sample. That is, the darkest green on the legend indicates a clear presence of urea, greater than 5 ppm.

Another embodiment is a kit for detecting DEF in fuel. The kit includes a buffered urease solution for reacting with a fuel sample for making a test solution and a pH adjustment solution for adjusting the pH of the test solution to basicity (pH of about 11). The kit optionally further includes a plurality of pH test strips for measuring the pH of the test solution, a plurality of heavy metal test strips for determining the presence of heavy metals in the test solution, and a plurality of reagent strips for reacting with the test solution and determining the presence of ammonia in the test solution. A color legend may be included for comparing the color change of the test solution after the reaction with the chemicals in the reagent strip. The kit may also include laboratory tools for storing the fuel sample and the test solution, such as, one or more of a test tube, a container, or a screw-cap vial, and one or more pipettes. The buffered urease solution comprises urease and sodium phosphate buffer, or about 100 ppm urease in about 0.10 M to about 0.050 M phosphate, buffered to a pH of about 6.8 to about 7.8, about 7.4 or about 7.6. The reagent strips may comprise solid bleach, an iron (III) cyano complex, and salicylic acid.

The terms used in this second embodiment have the same meanings as the terms defined above.

Example

Determination of Reagent Concentrations

Using a standard buffer formula table, a 200-mL batch of stock buffer solution was generated by dissolving 22.6 g of disodium hydrogen phosphate/dibasic sodium salt ($Na_2HPO_4$ (143 g/mol)) in 100 mL of distilled water. Then, 5.83 g of sodium dihydrogen phosphate ($NaH_2PO_4$ (129 g/mol)) was dissolved in another 100 mL of distilled water. The sum of the phosphate in both solutions is 0.20 mol. When the phosphate solutions are combined, 200 mL of 1.0-M phosphate buffer is created. The admixture of the phosphate solutions is designed to have a pH of 7.4.

0.05-M-0.20-M sodium phosphate buffer is a range of concentration commonly used with enzymes in an aqueous solution. 0.05-M sodium phosphate in commercially available distilled water with its pH adjusted to 7.4 is an appropriate buffer condition for the new reagent in the method of detecting DEF disclosed herein.

Because sodium phosphate dibasic is a majority of the phosphate reagent used in this bench-scale mixed-salt technique, it would be easier to use just the dibasic sodium salt ($Na_2HPO_4$ (143 g/mol)), make a titrimetric adjustment to a balanced pH of 7.4 with concentrated phosphoric acid ($H_3PO_4$, 85 wt %), and dilute the adjusted dibasic sodium salt to the final volume based on the sum total of phosphate in the solution.

The steps for making bulk amounts of the reagent include:
 a) filling a clean container with distilled water approximately up to the desired volume;

b) adding the correct mass (or the correct volume of a known concentration) of disodium hydrogen phosphate $Na_2HPO_4$;

c) adjusting the pH of the phosphate solution to 7.4 with an electronic pH meter by adding drops of concentrated phosphoric acid; and d) topping off the volume to achieve the correct concentration of 0.05-M in phosphate solution.

The above steps may be performed in just a few minutes to produce a large amount of the phosphate solution. Once produced, the bulk buffer solution may be stored indefinitely and dispensed as needed.

Next, the correct concentration of enzyme must be determined for the DEF detection method. A stock solution of 200 mg of the enzyme urease in 200 mL of the prepared phosphate buffer yields a 1 ppt (1000 ppm) w/v solution of buffered urease. This stock solution was used to make various dilutions (e.g., 1000 ppm, 100 ppm, 10 ppm, and 1 ppm), allowing a four order-of-magnitude range of observation across enzyme concentration. Then, a solution of 100 ppm urea in a volume of distilled water and a solution of 10 ppm urea in distilled water were prepared in a similar manner. There should be no hazard to aircraft engines or fuel systems with 10 ppm urea in water.

Determination of Detection Limits of DEF

An experiment was designed to test the different concentrations of urease (1000 ppm, 100 ppm, 10 ppm, and 1 ppm) against two urea levels (100 ppm and 10 ppm) with varying development times (10, 5, and 2 minutes). The development time is the time between urease first contacts the urea solution and the pH of the buffered urease solution is adjusted to 11 after urea converted to ammonia. The following procedures were taken for the experiment:

a) Using a pipette, 1.0 mL of each of the buffered urease solutions was transferred to its respective vial.

b) Immediately after performing step a), 1 mL of an aqueous urea sample was added to each of the buffered urease solutions.

c) Each of the mixed solutions was allowed to develop for a set time. The interval was stopped immediately by adding six drops of pH adjustment fluid. Each solution was tested against a chromatic pH paper to verify that its pH is 11.

Figure 2:
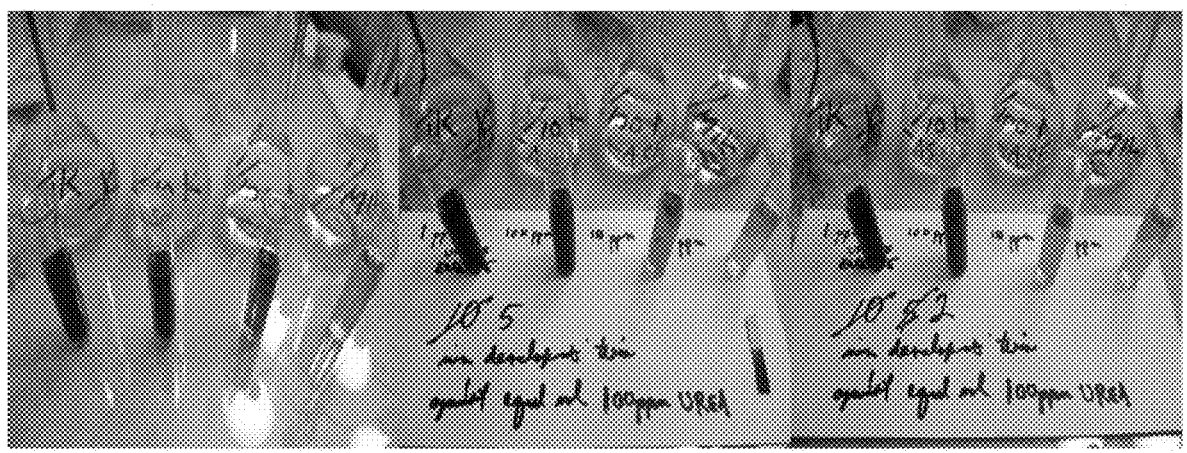
FIG. 2 is a color photograph showing the results of a urease concentration experiment in the Example.

100 ppm urea was subjected to treatment of 1.0 mL of buffered solutions, containing 1000 ppm, 100 ppm, 10 ppm and 1 ppm w/v urease from left to right in each photos shown in FIG. 2. From left to right, the experiments were conducted with 10 minutes, 5 minutes, and 2 minutes development times during which any urea present was converted to ammonia. The enzymatic conversion was stopped upon adjustment of the pH of the solutions to 11. As can be seen from FIG. 2, no additional benefit comes from having 1000 ppm urease, where one gets the same results as 100 ppm, with just the slightest difference in the 2 minute development time (right). In the 10 ppm urease, the response is slow and fades significantly with shorter development times. In the 1 ppm urease, there is simply not enough conversion for a distinct green color. Thus, 100 ppm w/v is recommended for urease concentration.

Figure 3:
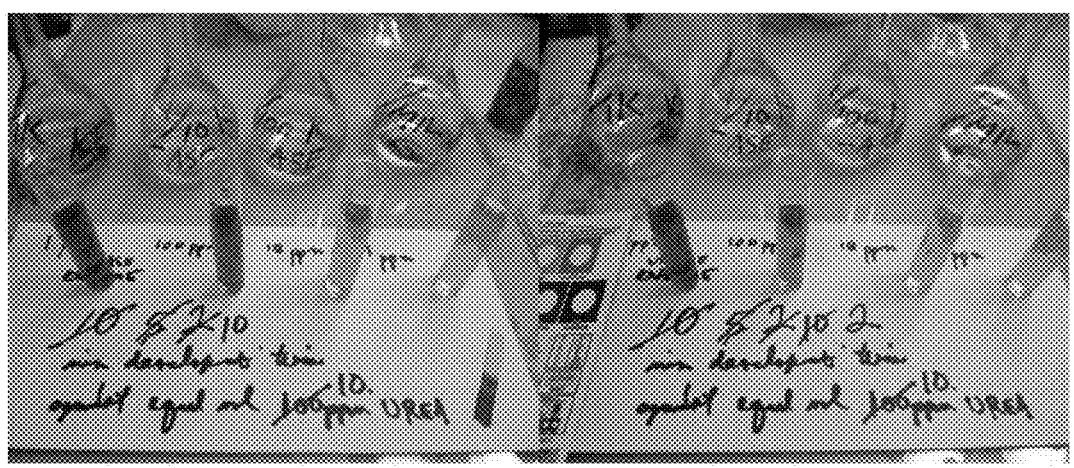
FIG. 3 is a color photograph showing the results of a urease detectability experiment in the Example.

For 10 ppm urea in water with 10 minutes development time, the 1000 ppm and 100 ppm test results are bright green as shown in FIG. 3. 10 ppm urea was subjected to treatment of 1.0 mL of buffered solutions, containing 1000 ppm, 100 ppm, 10 ppm and 1 ppm w/v urease from left to right vial in each photo in FIG. 3. From left to right, the experiments were conducted with 10 minutes and 2 minutes development times during which any urea present was converted to ammonia. The enzymatic conversion was stopped upon adjustment of the pH of the solutions to 11. In the 100 ppm urease case (second vial from the left in both photos in FIG. 3), the limits of indication for a sample in which 10 ppm urea (actually diluted down to 5 ppm urea and 50 ppm urease, with doubling of sample volume) is still strongly detected. Thus, the 100 urease solution is recommended with the development time of 5 minutes. This concentration of buffered urease allows for the detection of enough urea to dissolve in 2 mL of buffered solution to an effective concentration of 5 ppm urea. Therefore, as little as 5 ppm urea may be detected. The kit according to the present invention includes 100 ppm urease in 0.05-M phosphate buffered to a pH of 7.4 as the reagent. The reagent is capable of detecting 5 ppm urea in the test solution.

The above solution was used to test for the presence of ammonia. The test measures ppm urea which produces a trace (up to 5 ppm urea), positive (greater than 5 ppm urea), or negative (no urea) results. The trace, positive, and negative results are indicated with shades of green, dark green, and yellow, respectively.

Verification of Method in Aviation Fuel Sample

The determined solutions above were applied to an aviation fuel sample. A sample comprised of 10 ppm aqueous urea and house vodka (one-to-one ratio) was also tested for a realistic impure control against a false negative during the urea extraction phase of testing. The false negative may arise from alcohols in an aviation fuel.

The following procedures were taken for the test:

a) Added 1.0 mL of the buffered enzyme solution to a 10 mL screw-cap vial.

b) Added 5 mL of a commercial aviation fuel sample to the vial.

c) Capped the vial and agitated. The solution separated within 15 seconds and left it to stand for 5 minutes. (If any substance in the fuel kills the enzyme, there would be no conversion of urea to ammonia. Thus, there would be no formation of green color.)

d) Uncapped the vial, added 1.0 mL of 10 ppm urea to the vial, capped the vial, and agitated once again. The phases separated in 15 seconds or so.

e) Kept the solution capped and allowed it to develop for 10 minutes.

f) Adjusted the pH of the solution to 11, agitated the solution, and allowed the solution to separate once more.

g) Uncapped the vial, inserted a reagent test paper directly into the vial and agitated the solution mildly for 60 seconds.

h) Uncapped the vial.

i) Removed and discarded the reagent strip from the solution.

j) Carefully transferred the aqueous layer disposed in the bottom of the solution during development time (e.g., 10 minutes) to an observation vial.

k) Observed the color after three minutes.

Figure 4:
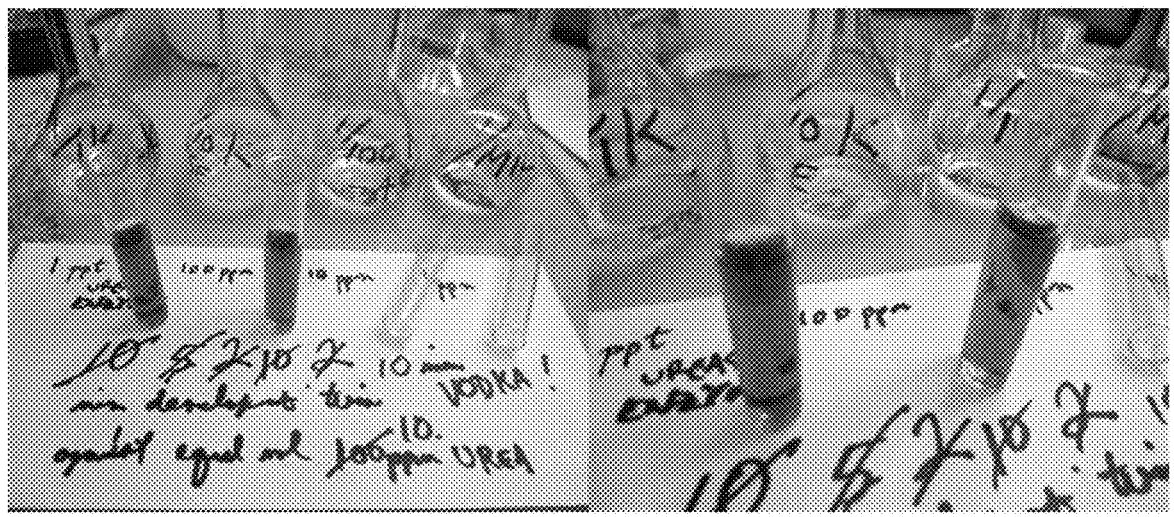
FIGS. 4 and 5 is a color photograph showing the results of a reaction of urease with alcoholic substances in the Example.
Figure 5:
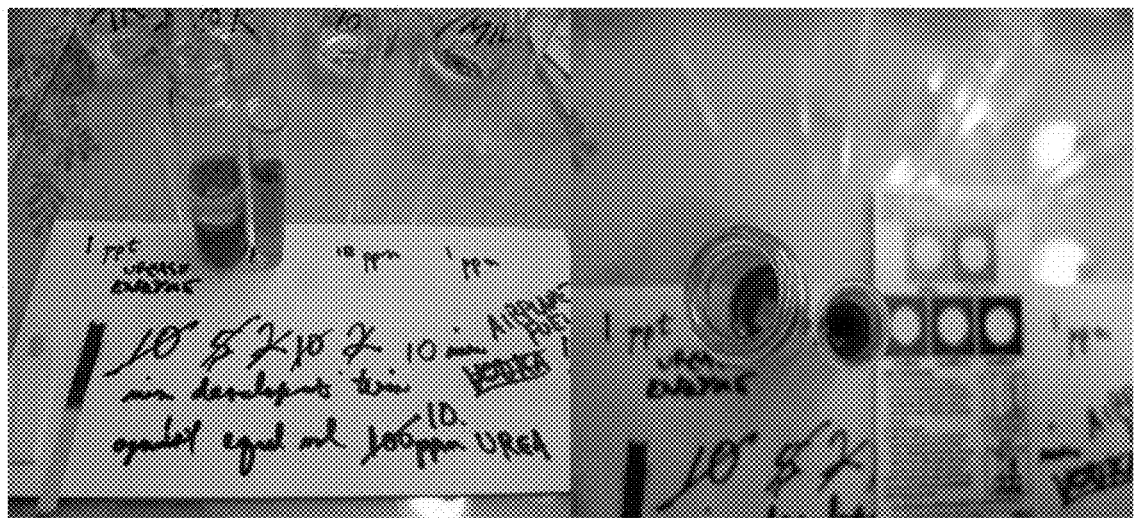

The results are shown in FIGS. 4 and 5. Referring to FIG. 4, each of 1.0 mL of 1000 ppm urease and 1.0 mL of 100 ppm urease were subjected to a mixture of 0.5 mL of 10 ppm urea and 0.5 mL of 86-proof vodka. As can be seen from the photos in FIG. 4, there is no loss in color going from the 1000 ppm to 100 ppm range of urease. There is no loss of color between purely aqueous urea and partially alcoholic urea.

Referring to FIG. 5, each of 1.0 mL of 1000 ppm urease and 1 mL of 100 ppm urease were subjected to a mixture of 0.5 mL of 10 ppm urea and 0.5 mL of 86-proof vodka. As can be seen from the photos in FIG. 5, there is no loss in color going from the 1000 ppm to 100 ppm range of urease. There is no loss of color between purely aqueous urea and partially alcoholic urea.

Figure 6:
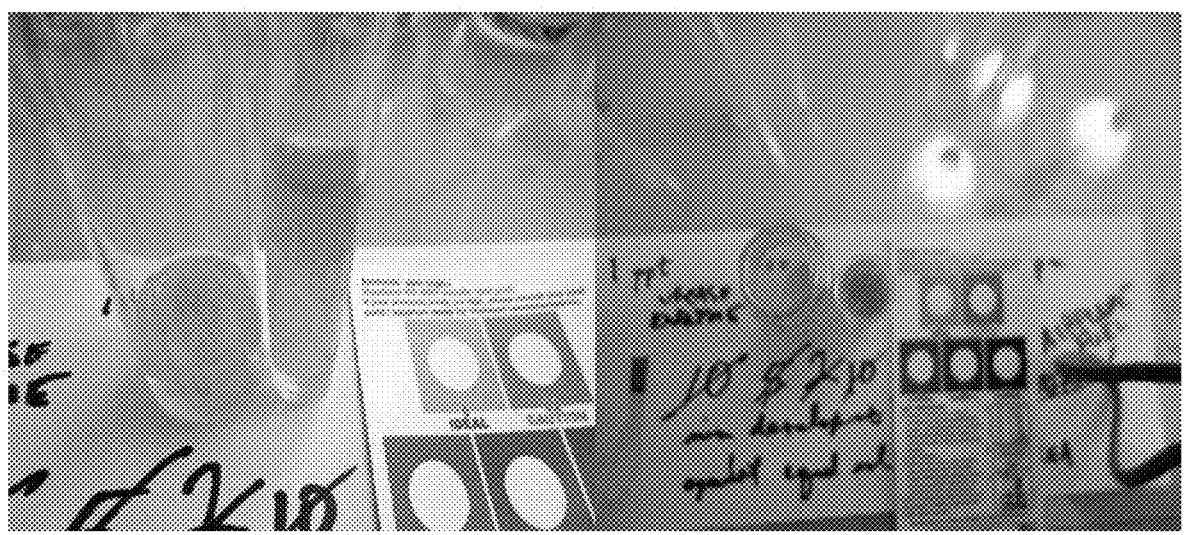
FIG. 6 is a color photograph showing the results of a reaction of urease with an airplane fuel with no urea added in the Example.

A fuel test without urea (a blank control) produced an expected response with no visible green coloration, as shown in FIG. 6. In FIG. 6, each of 1.0 mL of 1000 ppm urease and 100 ppm urease were subjected to the same sample of airplane fuel, with no urea added. The unadulterated fuel produced no green color.

Similarly, the alcohol control also tested positive for urea with the same level of color as the aqueous solution. As shown in FIG. 6, the new test worked in the fuel (in the presence of ethanol) with no indication of inhibited response.

From the experiment, it was discovered that the best time to separate the layers in the solution is after the pH adjustment to 11 and shake the solution. The aqueous layer is carefully transferred to the observation vial. The reagent strip is then added to the observation vial and is removed after 60 second.

Following controls were performed throughout the experiments:
- The entire suite of tests and water were tested for any indication of heavy metals. No heavy metals were detected. Commercially available distilled water was an acceptable solvent throughout the experiments.
- There was a week delay between the first tests and the tests that were reported described herewithin. No sign of degradation of enzyme activity in the urease solutions was detected after the interval had passed.
- No sign of the liberation of nickel (the active metal center in the enzyme) was detected after the first week.
- The indicating green color of the test persisted for numerous days. It was clear that the reaction was complete.

In general, the foregoing description is provided for exemplary and illustrative purposes; the present invention is not necessarily limited thereto. Rather, those skilled in the art will appreciate that additional modifications, as well as adaptations for particular circumstances, will fall within the scope of the invention as herein shown and described and of the claims appended hereto.

What is claimed:

1. A kit for detecting diesel exhaust fluid (DEF) in fuel, the kit comprising: a buffered urease solution having a pH of about 6.8 to about 7.8 which upon shaking with a fuel sample is configured to separate from the fuel sample into two or more layers including an aqueous layer; a pH adjustment solution configured to adjust the pH of the formed aqueous layer; and a plurality of reagent strips which when contacted with the aqueous layer are configured to detect the presence of ammonia in the aqueous layer.

2. The kit of claim 1, wherein the buffered urease solution comprises urease and sodium phosphate buffer.

3. The kit of claim 2, wherein the buffered urease solution comprises about 50 ppm to about 700 ppm urease in about 0.10 M to about 0.050 M phosphate.

4. The kit of claim 1, wherein the reagent strips comprise solid bleach, an iron (III) cyano complex, and salicylic acid.

5. The kit of claim 1, further comprising a plurality of heavy metal test strips.

6. The kit of claim 1, further comprising a color legend.

7. The kit of claim 1, further comprising one or more vials, and/or one or more pipettes.

8. The kit of claim 1, further comprising a plurality of pH test strips.

9. The kit of claim 1, wherein the pH adjustment solution adjusts the pH to greater than or equal to about 11.

10. The kit of claim 1, wherein the reagent strip causes a color change in the aqueous layer when ammonia is present.

11. The kit of claim 1, wherein the kit is configured to conduct tests for DEF".

* * * * *